United States Patent [19]
Sabban et al.

[11] Patent Number: 4,886,351
[45] Date of Patent: Dec. 12, 1989

[54] SCANNING CATADIOPTRIC OPHTHALMOSCOPE

[75] Inventors: Joseph C. Sabban, Orsay; Jean-Claude Rodier, Les Ulis; André Roussel, Brunoy; Jacques F. Simon, Paris, all of France

[73] Assignee: Centre National de la Recherch Scientifique, Paris, France

[21] Appl. No.: 246,013

[22] Filed: Sep. 14, 1988

Related U.S. Application Data

[63] Continuation of Ser. No. 673,842, Nov. 26, 1984, abandoned.

[30] Foreign Application Priority Data

Nov. 21, 1983 [FR] France ............................... 83 18512

[51] Int. Cl.$^4$ ............................................. A61B 3/10
[52] U.S. Cl. ..................................... 351/221; 351/205
[58] Field of Search ............... 351/205, 206, 211, 212, 351/221

[56] References Cited

U.S. PATENT DOCUMENTS 3,698,099 10/1972 Matsura ................................... 351/6
4,003,642 1/1977 Vogeley ............................. 351/205
4,091,814 5/1978 Togo .................................. 128/303.1
4,213,678 7/1980 Pomerantzeff et al. ................ 351/7
4,620,318 10/1986 Hill ...................................... 351/221

FOREIGN PATENT DOCUMENTS 0223356 5/1987 European Pat. Off. ............ 351/221
0044770 1/1982 France .

OTHER PUBLICATIONS

IEEE Transactions on Biomedical Engineering, vol. BME-28, No. 7, Jul. 1981, IEEE, New York (US), R. H. Webb et al., "Scanning Laser Ophthalmoscope".
Republique Francaise Search Report, completed Sep. 4, 1984, by Examiner K. D. Rieb, Institut National de la Propriete Industrielle.
Springer-Verlag Berlin Heidelberg, "Physiological Optics" 1980, pp. 292–294, New York.

Primary Examiner—Bruce Y. Arnold
Assistant Examiner—P. M. Dzierzynski
Attorney, Agent, or Firm—Staas & Halsey

[57] ABSTRACT

A scanning ophthalmoscope comprises eye illuminating means comprising a light source block (A), an outward refraction compensator (Ba), scanning means (C) suitable for deflecting a beam produced by the light source block over a raster of lines, and a catoptric ophthalmoscope per se (D) for transmitting the deflected light beam into the eye through the pupil thereof. Light returns along the same path to a partially reflective beam separator plate (L$_1$), it then passes through a return refraction compensator (Br) followed by a detector (E) and an electronic processing circuit (F). The outward and return paths are kept highly symmetrical. The catoptric ophthalmoscope (D) is essentially constituted by a spherical mirror (M$_1$). The scanning mirrors (M$_3$ and M$_4$) pivot about respective axes which are colinear with the focal axes of the astigmatism which the spherical mirror produces in the image of the spot of a patient's pupil.

19 Claims, 5 Drawing Sheets

SCANNING CATADIOPTRIC OPHTHALMOSCOPE

This is a continuation of co-pending application Ser. No. 673,842 filed on Nov. 21, 1984 now abandoned.

BACKGROUND OF THE INVENTION

1. Field of the Invention

The invention relates to techniques for examining the eye, and in particular the back of the eye.

2. Description of the Related Art

The instruments used for this purpose are generally called ophthalmoscopes and serve to perform various different kinds of examination: these begin with simple observation of the retina and extend to more sophisticated applications such as fluorescent angiography, mono and polychromatic examinations, and micro-ophthalmoscopy. For conventional examination of the retina, this type of ophthalmoscopy is performed with a medium field of 20° to 30°. Finally, whatever the application, the level of performance obtained by an ophthalmoscope is essentially defined by its resolution.

The highest performance instruments currently available are retinographs which combine an ophthalmoscope with a camera. These do not provide direct observation, and they are difficult to adapt to dynamic observation of the retina since they are technically limited to taking 3 or 4 photographs per second.

Further, in current ophthalmological practice, ophthalmoscopes are expected to obey Gullstrand's rule.

The application of this rule consists in using different parts of the cornea and the lens of the eye for illumination and for observation respectively. This rule limits resolution and the possibility of observing small details.

A few years ago, experiments were performed to try to associate a vidicon tube with a retinograph in order to display retina structures on a television screen. These experiments did not provide the hoped-for results, in particular because the resolution obtained was small compared with that obtained from a retinographic photograph.

More recently, U.S. Pat. No. 4,213,678 in the names of Pomerantzeff and Coll has proposed a scanning ophthalmoscope. This instrument transposes the flying spot technique used in television, in which a transparent object (eg. a frame of a movie reel) is electronically scanned at television standards. This U.S. patent teaches the use of completely optical scanning using mechanical means to deflect a light beam such as a laser beam in two dimensions through an instrument aperture which is small in comparison with the pupil of the eye. The instrument then collects the optical signal as reflected from any point at full aperture regardless of the incidence, ie. the instrument's field of view is typically 30°.

In application of Gullstrand's rule, this prior art ophthalmoscope suffers firstly from the limitation imposed on its resolution by the use of the instrument's small illuminating aperture, and secondly from the use of an observation beam collector which is responsive to the instantaneous beam in the entire field of the instrument. This makes the instrument highly sensitive to reflections and to spurious light, and the above-mentioned U.S. patent seeks to remedy this defect by various optical means, such as the use of polarized light.

SUMMARY OF THE INVENTION

The present invention provides a scanning ophthalmoscope of different structure which is capable of attaining improved performance levels.

A first aim of the invention is to provide a scanning ophthalmoscope which does not obey the above-mentioned Gullstrand rule as is generally applied in conventional ophthalmoscopes.

Another aim of the invention is to provide a scanning ophthalmoscope having a light beam of small extent, both on its outward or illuminating path and on its return or observation path.

Another aim of the invention is to provide a scanning ophthalmoscope using, in the immediate vicinity of the eye, catoptric type light transmission means, ie. means essentially constituted by mirrors.

Another aim of the invention is to use a spherical mirror in said transmission means, with the astigmatism thereof, relative to the pupil of the patient under a non-zero angle of incidence, being compensated by a special adaptation of the scanning means.

Another aim of the invention is to use means for transmitting light to the eye of the patient and scanning means which are in common for the outward illumination path and for the return observation path so as to reduce light interference.

Another major aim of the invention is to enable microscopic examination of the retina.

Another aim of the invention is to compensate for any ocular ametropia that may be present in the patient, in order to obtain high quality images at large pupil apertures.

Yet another aim of the invention is to stabilize the return beam intended for observation, thereby enabling its geometric extent to be highly reduced, while nevertheless enabling a large field to be observed at the back of the eye.

In known manner, the proposed scanning ophthalmoscope comprises means for illuminating the eye, which means include a light source block, scanning means suitable for deflecting the beam produced by the light source over a raster of lines, and optical means for transmitting the deflected light beam to the eye through the pupil of the patient; means are also provided for observing the eye as illuminated in this manner.

In general terms, the improvement of the present invention lies in the illumination means and the observation means sharing the same scanning means and optical means for transmitting light to and from the eye; in addition the observation means have a small detection diaphragm conjugated with the point source produced by the light source block, and have an aperture slightly larger than the size of the image of said point source, together with photoelectrical transducer means such as a photomultiplier placed downstream from the said diaphragm.

This arrangement makes it possible to use a light beam of small extent both during the outward illumination path and during the return observation path.

Advantageously, the optical means for transmitting light to the eye are of the catoptric type, ie. they are essentially constituted by mirrors. For various reasons, persons skilled in the art have up to now only used dioptric optical systems, even for the portion of the ophthalmoscope which is close to the eye. The use of catoptric means makes it possible to eliminate spurious images that dioptric systems generate. It has turned out to be possible to compensate the astigmatism found in catoptric systems, as is explained below.

Preferably, the compensation is performed in accordance with the invention as follows: the optical means for transmitting light to and from the eye comprise a spherical mirror which used at non-zero incidence. The scanning means include two controlled light beam deflectors, operating about respective axes which are co-linear with the focal axes of the astigmatism produced by the spherical mirror on the spot image of a patient's pupil, given the non-zero incidence.

In a particular embodiment, the two controlled deflectors are pivoting mirrors.

A light beam separator such as a separator plate may be placed upstream from the scanning means along the illuminating beam in such a manner that the illuminating beam is reflected by the beam separator while the observation beam passes therethrough. It is then desirable to conserve functional symmetry between the outward illumination path and the return observation path, outside their common portion.

To this end, it is advantageous for the ophthalmoscope to include two similar refraction compensators, one placed on the illumination path upstream from the separator and the other placed on the observation path downstream from the separator. This makes it possible to correct for the patient's ametropia (if any), which correction is desirable when working with the patient's pupil at large aperture.

In one embodiment, each compensator comprises a fixed lens, a carriage bearing a moving lens, and a diaphragm acting as an inlet stop, with the carriages of the two compensators moving together.

Merely changing the lens placed at the inlet of the compensator provided on the outward illumination path makes it possible to perform either small field scanning retina microscopy or else as a medium field observation, with the refraction-compensating diaphragms being adjusted accordingly.

The light source block may be constituted by a laser or by an arc lamp together with optical focusing means for generating a point light source. The point source is applied to the refraction compensator via the interchangeable lens. The beam from the original light source is conveyed to the point source derived therefrom by an optical fiber, at least for medium field work. It is thus possible to physically separate the light source per se from the portion of the ophthalmoscope which comes close to the patient.

On the return observation path, a detection lens is placed immediately upstream from the above-mentioned small detection diaphragm, which is itself placed at the focus of the lens and is followed by a photodetector.

The faster of the two deflectors performs line scanning and is driven in an oscillatory manner so as to produce sinusoidal scanning. In addition the ophthalmoscope includes electronic means suitable for digitizing the output from the detector and for filling two digital memories in reverse order with the signals detected during the forward and backward portions of the sinusoidal period. Preferably the output from the photodetector is sampled at a varying rate as a function of the excursion speed of the sinusoidal scan.

BRIEF DESCRIPTION OF THE DRAWINGS

An embodiment of the invention is described by way of example with reference to the accompanying drawings, in which.

DESCRIPTION OF THE PREFERRED EMBODIMENTS

Figure 1:
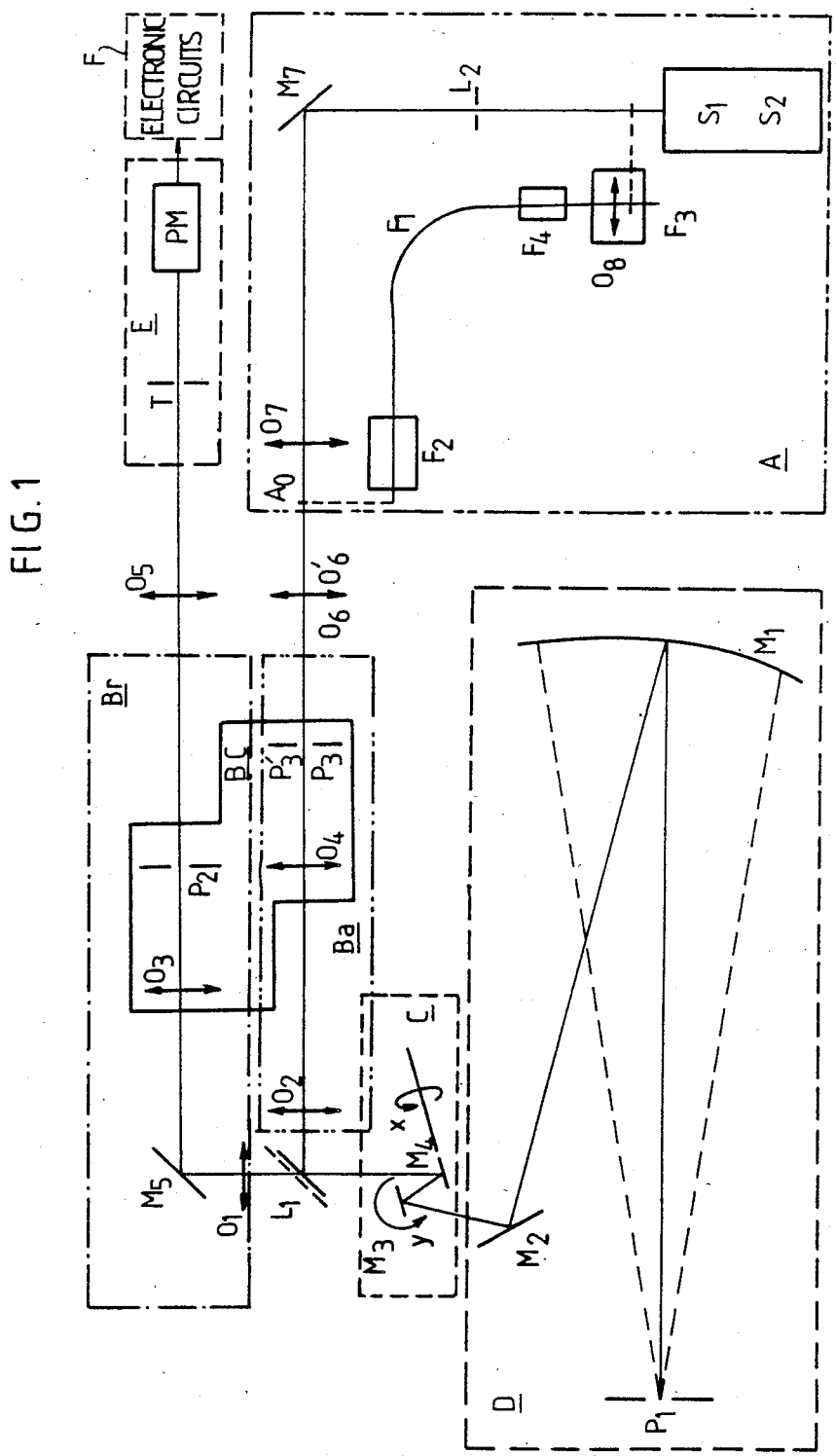
FIG. 1 is an overall view of the various functional blocks constituting on embodiment of the an ophthalmoscope in accordance with the invention.

The ophthalmoscope shown in FIG. 1 comprises the following subassemblies:

a light source block A;
an outward refraction compensator Ba;
a scanner subassembly C;
means for transmitting light to the eye, hereinafter referred to as the catoptric ophthalmoscope D, given that its design is based on mirrors;
a refraction compensator Br on the return observation path;
a measurement and detection block E; and
electronic circuits F.

This structure is capable of providing a television image of any region of the retina, or more generally the interior of the eye.

In the light source block A, the original light beam is produced either from a low-power laser $S_1$, or else by a xenon arc lamp $S_2$. The function of this block is to generate a point of light from the original beam such that the geometrical and spectral characteristics of the point are defined by the particular application intended: eg. fluorescent angiography; mono or polychromatic examination; micro-ophthalmoscopy; or medium field (20° to 30°) ophthalmoscopy.

When the optical scanning ophthalmoscope is being used for medium field examination, it is advantageous for the source block A to be made from an optical fiber $F_1$, having a core diameter of 6 microns for example. The optical fiber is held in place by fasteners $F_2$, $F_3$, and $F_4$. A lens $O_8$ focuses the original beam to give it the desired geometrical characteristics. The source (laser or arc) may thus be mechanically dissociated from the rest of the optics, and the entire assembly can thus be considerably lightened giving rise to an ophthalmoscope per se which is of considerably reduced bulk.

A variant is suitable for all applications. The beam from the source $S_1'$ or $S_2$ is applied to a 45° deflector mirror $M_7$ which reflects the beam towards a microscope lens $O_7$ similar to the lens $O_8$ on the other path. If a laser is being used, it is advantageous to interpose a purifying diaphragm $L_2$ on the path of the laser beam.

A laser beam in association with a filter hole makes it possible, in particular, to offer the necessary optical resolution for operating in microscope mode while scanning the retina. The scanned field is then reduced (6° to 8°).

In both cases, an elementary examination spot $A_0$ is obtained at the output from the light source block A, and is hereafter referred to as a point source.

The following description is given in terms of the most frequent kind of examination which is of the retina itself, rather than of some section plane through the interior of the eye in front of the retina.

If the patient is suffering from ametropia (spherical or cylindrical) the point source delivered by the block A does not necessarily correspond (in position and in associated wave surface) with an optical conjugate of the retina to be examined. The refraction compensator Ba serves to compensate for any ametropia.

Prior to the compensation per se, the point source $A_0$ is applied to a lens $O_6$ which focuses it at infinity, thus producing a beam of parallel rays. For retina microscopy, a microscope objective is used for the lens $O'_6$ giving magnification of about twenty times.

In the embodiment shown, the refraction compensator per se begins with a diaphragm $P'_3$ or $P_3$ which has an aperture of 3 mm or of 1 mm depending on whether retina microscopy or medium field observation are being performed. Then there is a lens $O_4$. The lens $O_4$ and the diaphragm $P_3$ or $P'_3$ are movable together in axial translation along the beam on a carriage BC. Further on, another lens $O_2$ identical to the lens $O_4$ picks up the beam. The diaphragms $P_3$ or $P'_3$ are placed at the object focus of the lens $O_4$. This lens thus receives a parallel beam of light from the point source $A_0$ of variable area depending on the diaphragm $P'_3$, $P_3$ and the intended application. By moving the carriage BC, the point source is moved to a position which corresponds to proper focusing on the retina. Correction of a patient's astigmatism is obtained by adding cylindrical lenses from a conventional lens box, and placed in the vicinity of $P_3$ or $P'_3$.

The essential function of the lens $O_2$ is to form at its focus a real image of the pupil adjacent to the pair $M_3$, $M_4$ described below. The pair $O_4+O_2$ thus provides transport of the pupil at unity magnification.

At the output from the outward refraction compensator Ba, the light beam arrives at a separation plate $L_1$ which reflects at 45° towards the scanning means C.

The symmetry between the outwards refraction compensator Ba and the return refraction compensator Br should be observed straight away. From the separator plate $L_1$, which is passed both outward bound and on return, the return beam first meets a lens $O_1$ identical to the lens $O_2$, then a 45° deflector mirror $L_5$. Thereafter, in reverse order, it passes through a lens $O_3$ and a diaphragm $P_2$ which are both mounted on the same carriage BC as the lens $O_4$ and the diaphragm $P_3$ or $P'_3$ and which are identical thereto. If necessary the diaphragm $P_2$ is provided with a cylindrical lens corresponding to the cylindrical lens used at $P_3$ or $P'_3$. Thus, at the output from the return refraction compensator Br, there will be a beam of parallel rays which has been subjected to exactly the same optical treatment as the outward path from downstream of the lens $O_6$ or $O'_6$. The outward path and the return path are thus indeed symmetrical.

It is now possible to deal with the optical path going downwards in the drawing from the separator plate $L_1$, without it being necessary to distinguish between the outward and the return paths.

After reflection from the separator plate $L_1$, the optical path encounters two mirrors $M_3$ and $M_4$, which reflect the light beam about two perpendicular directions, so as to construct a raster scan of parallel lines similar to the raster produced by an electron beam in a television tube. For example, in this manner it is possible to scan 25 images of 625 lines each (European TV standard).

The plane mirror $M_4$ is fixed to a resonant electromechanical system for line scanning by pivoting about an axis of rotation x. (In a variant, a polygonal mirror rotating at constant speed could be used). The plane mirror $M_3$ is driven in asymmetrical sawtooth oscillations by a servo-controlled galvanometer and picks up the line scan to turn it into a raster or, in other words, a two dimensional scan.

The beam deflected in this manner is applied to the catoptric ophthalmoscope D. The ophthalmoscope begins with a plane mirror $M_2$ to fold the beam in order to provide sufficient space for meeting the practical and ergonomic requirements of peripheral retina observations. The essential part of the ophthalmoscope D is a spherical mirror $M_1$ whose function is to conjugate the pupil with the flying spot produced by the retina scan.

Up to the present, ophthalmoscope instruments have used dioptric optical systems giving rise to spurious images due to reflections on the boundaries of the lenses therein. The reason for this has certainly been the above-mentioned Gullstrand rule, which is traditionally applied in ophthalmology.

The present invention goes directly against this tradition, and does not apply Gullstrand's rule. It does the opposite: in the vicinity of the eye it uses a common optical path both for the outward illuminating beam and for the return observation beam.

The invention also makes use of a catoptric ophthalmoscope in spite of the astigmatism inherent in the use of a spherical mirror used at non-zero incidence. It has been observed that this astigmatism can be compensated.

A simple way of doing this is to make the mirrors $M_3$ and $M_4$ pivot about respective axes which, taking account of the reflection at $M_2$, are colinear with the astigmatic lines of focus produced by the spherical mirror on the spot image of a patient's pupil (ie. reduced to its central point). Thus, by producing an effect equivalent to astigmatism, the proposed scanning system considerably reduces aberrations at the pupils. This is true both for the outward path and for the return path. Another advantage drawn from this disposition is that after returning and leaving the scan means C a second time, the observation light beam is stationary. This facilitates detecting the information coming from the illuminated point on the retina.

After passing back through the separator plate $L_1$, the fixed observation beam passes back through the refraction compensator Br which is identical to the compensator Ba and which has the same cylindrical correction lenses. As mentioned above, the moving carriage BC ensures that the same cylindrical and spherical corrections are applied in both compensators. It is capable of correcting ametropia over a range of at least 15 diopters spherically and up to at least 5 diopters cylindrically. An image is thus finally obtained of the flying spot on the retina, which image is completely fixed both in direction and in position, regardless of the patient's ametropia in these ranges.

A lens $O_5$ is placed at the output of the return refraction compensator Br which thus forms at its focus a real, stationary and quasi point image of the flying spot in the scanned field of the retina.

The detector block thus comprises a small diaphragm T placed in the plane of said stationary and quasi point image of the retina so as to perform space filtering of the information and thus remove spurious light returned by the system and due essentially to the front regions of the eye (cornea and lens).

The instantaneous field of observation is thus delimited by the diaphragm T.

A photodetector, preferably a photomultiplier, is then placed downstream from the diaphragm. Although the position of the photodetector on the optical axis is not critical, it is possible to place it in the image plane of the pupil given by a field lens placed behind the diaphragm T. The field of observation is then reduced to the instantaneous field of the scan point. Naturally the size of the photodetector's sensitive surface is also chosen to correspond to the size of the image of the patient's pupil. This ensures a considerable reduction in the quantity of spurious light collected, and consequently provides a considerable increase in the signal to noise ratio, thereby improving the overall qualiity of the ophthalmoscope.

The output signals from the photomultiplier PM are then applied to electronic circuits F which are described below. These circuits are naturally connected to the oscillating scan mirrors $M_3$ and $M_4$ to ensure synchronization between the optical scanning and the scanning signals applied to a TV monitor on which the image of the retina is reproduced.

Figure 2:
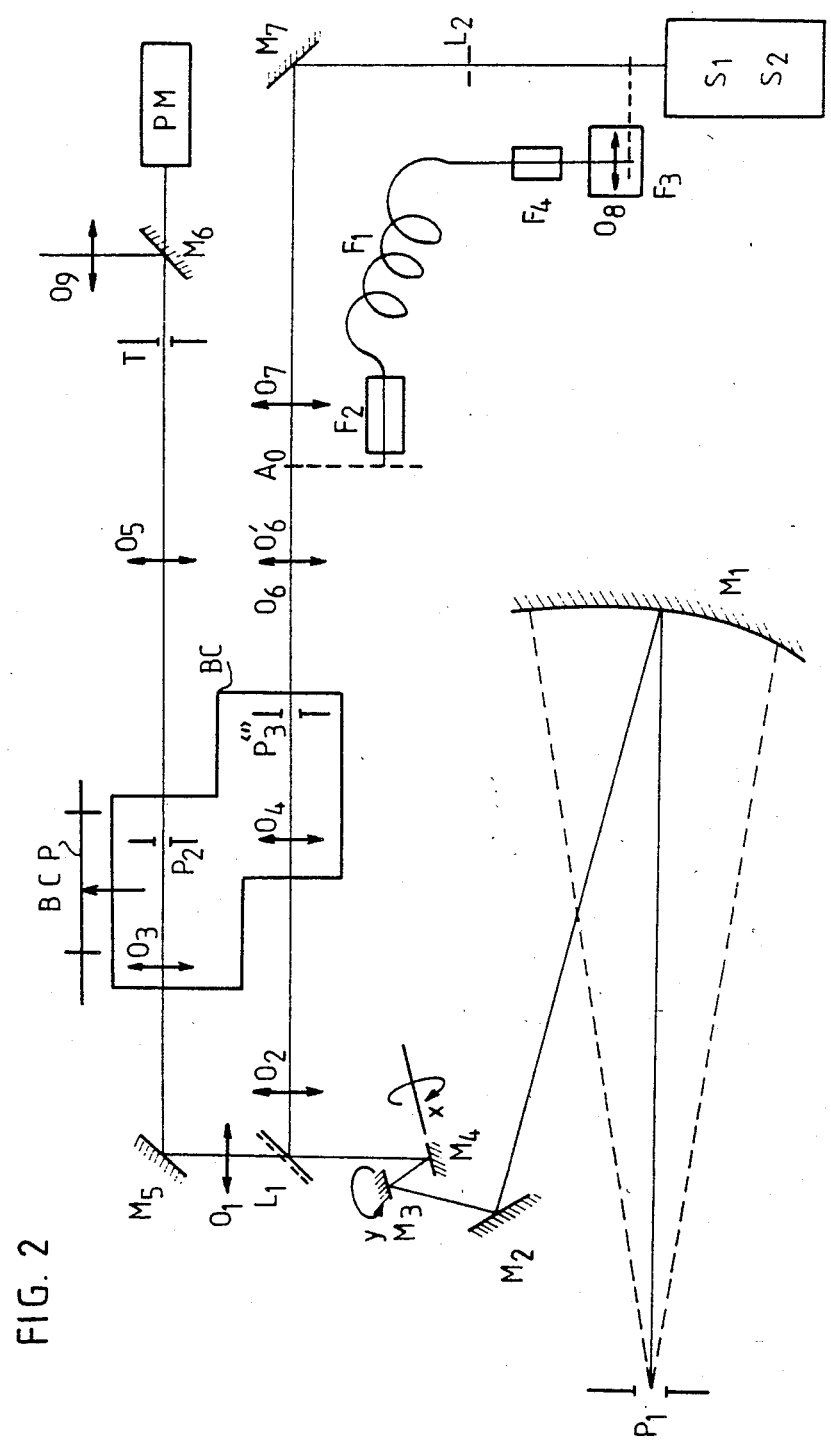
FIG. 2 is a more detailed view of the FIG. 1 ophthalmoscope.

Brief comments on FIG. 2 are now appropriate. There is little difference from FIG. 1. In particular it may be observed that the use of an optical fiber $F_1$ makes it possible to separate the source per se from the rest of the instrument.

The association of the carriage BC of the two refraction compensators with an indicator unit such as a potentiometer sweep arm BCP enables the operator to be shown the strength in diopters of the spherical correction currently being applied. The cylindrical correction is applied by means of lenses taken from a box in the conventional ophthalmological manner, and placed close to the two diaphragms $P_2$ and $P_3$ (or $P'_3$).

A final difference between FIGS. 1 and 2 should be observed: between the small output diaphgram T and the photomultiplier PM a partially reflective and/or wavelength selective mirror $M_6$ is placed to deflect the beam to a lens $O_9$, eg. for direct display or observation of the image of a point of the retina or to measure the intensity of the received beam. In known manner, the intensity of the emitted beam may be obtained from the quantity of light passing directly through the separator plate $L_1$.

The following detailed description concerns the sinusoidal scanning produced by the mirror $M_4$. Such sinusoidal optical scanning is illustrative in FIG. 3.

During the portion AB of the rising half period of the sinusoid, a memory $M_1$ filled with samples of the detected signal, as obtained from the output from the photomultiplier PM. During the immediately following falling half period CD, a memory $M_2$ is filled. However, the memory $M_2$ is filled in reverse address order relative to the order in which the memory $M_1$ is filled. Thereafter, in the following rising half period EF, the memory $M_1$ is filled again, and so on.

The memories are read as follows: while the memory $M_2$ is being filled, the information previously stored in the memory $M_1$ is read, in the usual address order. While the memory $M_1$ is being filled a second time (period EF), the contents of the memory $M_2$ is read in normal address order, ie. in the reverse order to the order in which the memory $M_2$ was filled. This results in line scanning in the normal order for TV standards with all the lines being scanned in the same direction for read out. A simple variant would be to fill both memories in address order and then to read the memories in opposite orders.

The line scan half period is thus synchronized with a video line. The sinusoidal horizontal video scan frequency is thus 8 kHz. This is then converted to the TV standard of twenty-five 625-line frames per second. The frame scan rate is 50 Hz in the conventional manner using sawtooth scanning signals, and successive odd and even frames may be interlaced.

Finally, the output signal from the photodetector PM takes place at an instantaneous rate proportional to the horizontal scan rate, thereby compensating for the distortion due to the sinusoidal scane.

Figure 4:
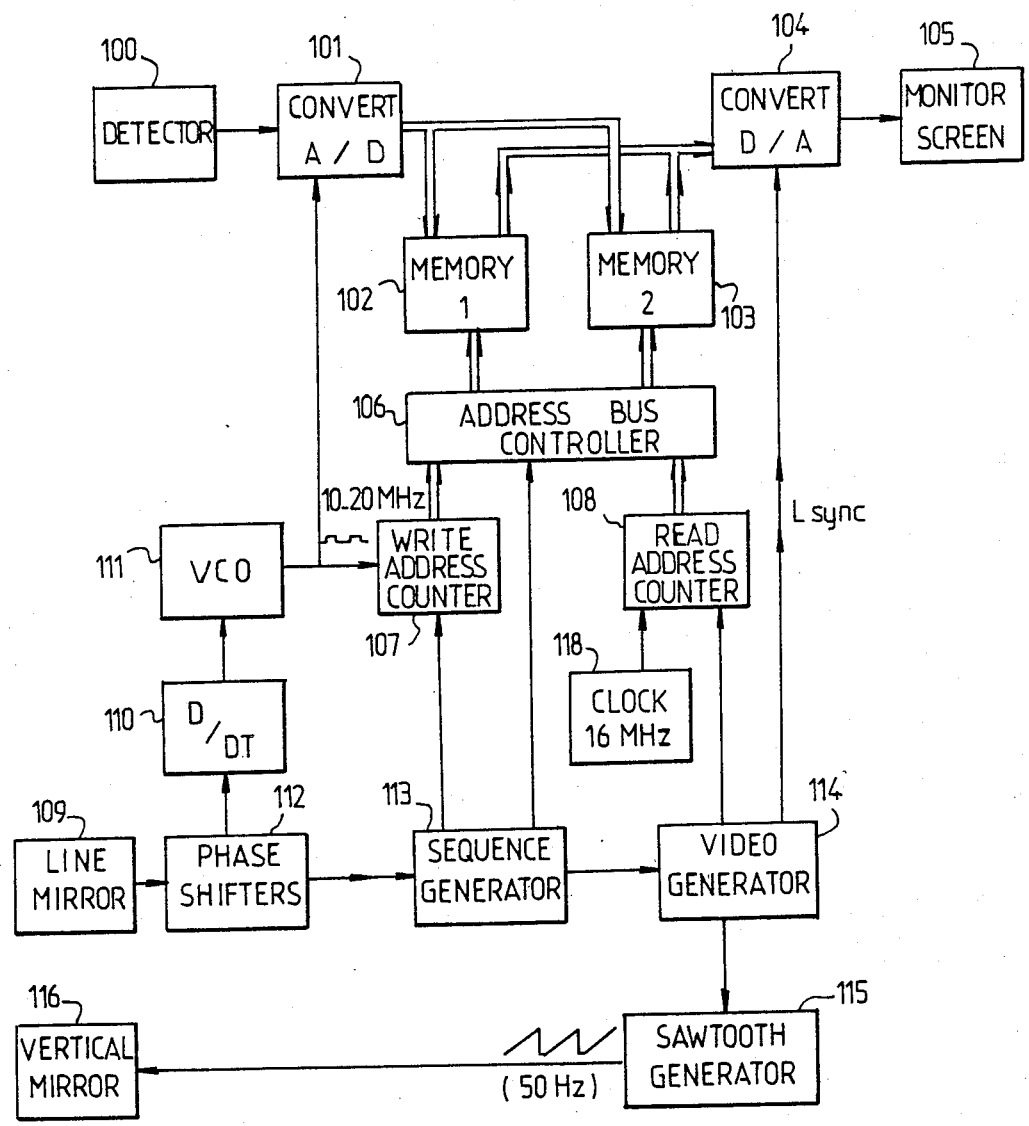
FIG. 4 is a block diagram of the electronic circuits of an ophthalmoscope in accordance with the invention.

Reference is now made to FIG. 4. The photodetector PM is now given the reference 100. Its electrical output signal is applied to an analog to digital converter 101 which also has a sampling control input.

As indicated above, the line deflection mirror (now referenced 109) oscillates at 8 kHz. It thus provides the reference for position and for synchronization. It is provided with a transducer giving an indication of its position in electrical form. Given the resonant nature of the line deflection mirror control, there may be an offset between the real position of the mirror and the position indicated by the electrical signal. The signal is therefore applied to a phase shifter network 112 with the primary function of compensating any such offset between the real mirror position and the position indicated by the signal. The phase shifters in the network are also arranged to determine the points A, B, C, and D as shown on FIG. 3. The person skilled in the art will understand that this can be performed by means of phase shifters applying various delays to the sinusoidal signal followed by respective comparators.

A signal which has been corrected for the offset only by means of a first phase shifter in the network 112, and thus indicative of the real position of the mirror, is applied to a differentiator circuit 110 which has the effect of phase shifting the input sinusoidal signal by $\pi/2$. The differentiator 110 may thus be a simple phase shifter. The output signal from the differentiator 110 is a voltage proportional to the instantaneous speed of rotation of the line mirror, and this voltage is applied to control a voltage controlled oscillator (VCO) 111. The VCO 111 then delivers a clock signal at frequencies in the range 10 MHz to 20 MHz, which frequencies are proportional to the rotational speed of the line mirror. This clock signal is applied to a write address up/down counter 107 and to the sample control input of the analog to digital converter 101.

A second up/down counter 108 is used for read address counting, but it is used in up mode only.

Figure 5:
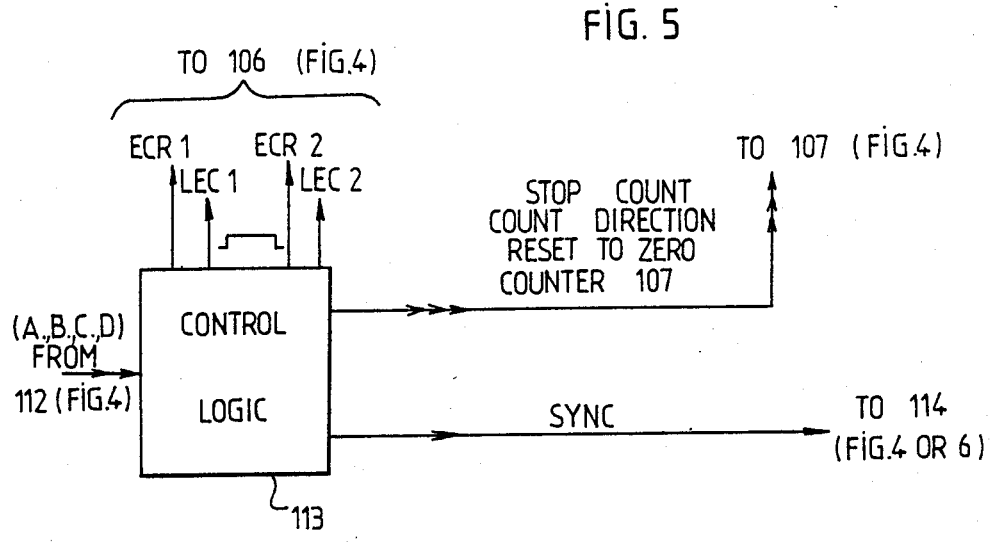
FIGS. 5 and 6 show blocks 113 and 114 of FIG. 4 in greater detail.

Reference is now made to FIG. 5.

Figure 3:
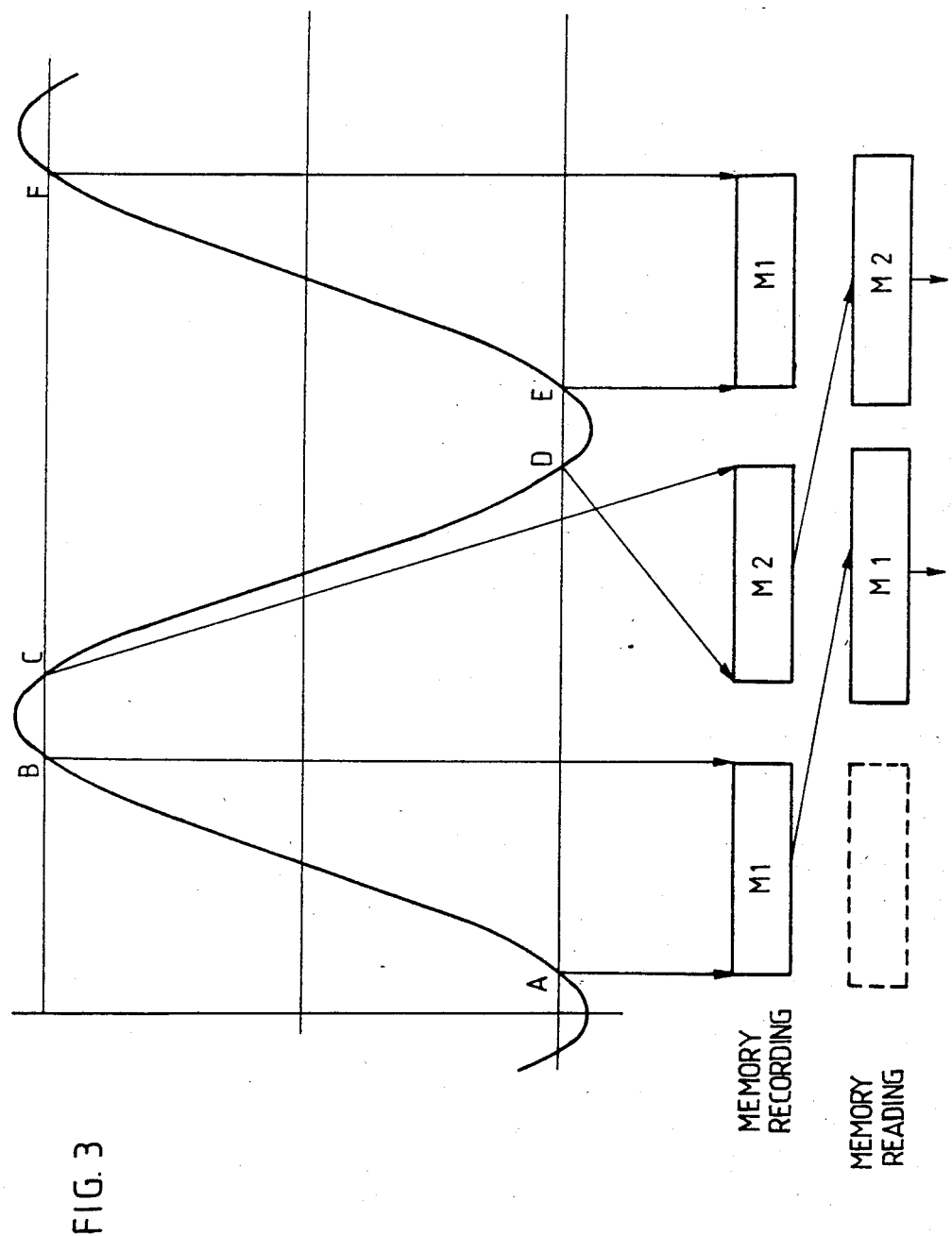
FIG. 3 is a timing diagram showing how the digital memories are filled as a function of the sinusoidal scan, and how they are read.

Data representative of the time positions of the points A, B, C, D in FIG. 3 is applied to a sequence generator 113. The sequence generator is essentially a logic control circuit and it serves to generate signals $ECR_1$, $LEC_1$, $ECR_2$ and $LEC_2$, on the basis of said signals A, B, C, D. The ECR signals control writing, the LEC signals control reading, and the subscript indicates which memory (1 or 2) is concerned.

The control logic circuit also supplies other signals for stopping and resetting to zero the write address up/down counter 107 and also for setting the appropriate count direction to perform the operations described with reference to FIG. 3. Finally, the logic control circuit supplies a signal SYNC for synchronizing a video generator 114 (see FIGS. 4 and 6) on the mid points of segments such as BC and DE (see FIG. 3).

Figure 6:
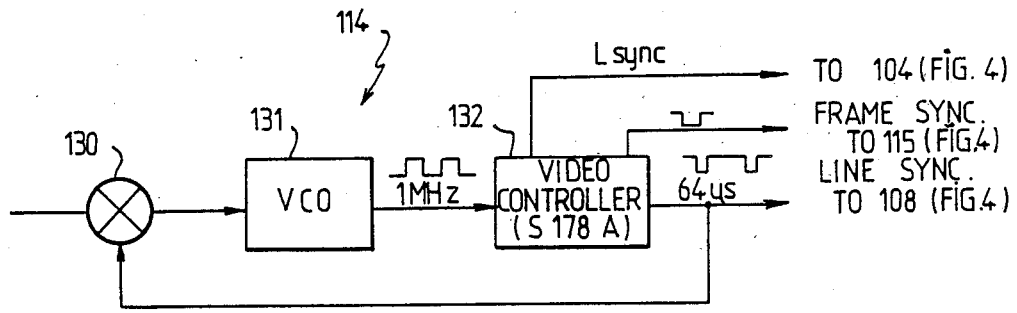

A more detailed diagram of the video generator 114 is given in FIG. 6. The video generator comprises a phase-lock loop for synchronizing the video lines with the horizontal scan. It is constituted by a phase comparator 130 having a first input connected to receive the signals from the control logic circuit 113 and a second input connected to receive signals from a video controller 132. The output from the phase comparators 130 is applied to control a second VCO 131 operating at a normal frequency of 1 MHz, and delivering squarewave output signals. These are applied to the video controller 132 which may be in the form of a commercially available integrated circuit intended for supplying the conventional video control signals, ie. the following CCIR standard synchronizing signals: line sync. frame sync. and combined line and frame sync. The pure frame synchronizing signals are applied to a sawtooth generator 115 (see FIG. 4), and the pure line synchronizing signals are applied to the read address up/down counter 108.

The sawtooth generator 115 may be an integrator which is reset by the frame synchronizing signals and which provides the asymmetrical sawtooth signals for driving the vertical deflection mirror referenced 116 in FIG. 4.

The address up/down counter 108 normally operates at a fixed clock frequency of 16 MHz as defined by a clock 118. It is reset to zero by each line sync. signal supplied by the video generator 114.

The four read/write control signals $ECR_1$, $LEC_1$, $ECR_2$ and $LEC_2$, supplied by the sequence generator 113, and the address signals suppled in parallel to the outputs from the counters 107 and 108 are applied to an address bus controller 106 to perform appropriate addressing in the first and second memories referenced 102 and 103 respectively.

More precisely, the write address up/down counter 107 changes the write address applied to the first memory 102 in ascending order and at varying speed while the counter 108 varies the read addresses applied to the second memory 103 likewise in ascending order, but at constant speed.

Then, in preparation for the following phase, the two counters exchange memories which they address, the up/down counter 107 is stopped at its high address from the previous cycle, while its count direction is reversed, and the counter 108 is reset to its low value and its count direction is not reversed. Thus during the said following phase, the up/down counter 107 changes the write address applied to the second memory 103 in the descending order and at variable speed, while the counter 108 changes the read addresses applied to the first memory 102 in ascending order at a constant rate.

The read/write functions described with reference to FIG. 3 for the first and second memories are thus obtained.

The data signals delivered alternately by one memory and then the other are applied to a digital to analog converter 104 which also receices the combined sync. signals Lsync from the video generator 114. The output from the converter 104 then provides all the signals required for controlling a conventional TV monitor screen 105.

There follows a detailed list of the components used in a specific embodiment of the invention.

Light source block A
$S_1$=a Spectra Physics argon laser at 488 nm (blue), or at 514.5 nm (green); or a Hughes He-Ne laser at 632.8 nm;
or $S_2$=a Cermax Xe Illuminates xenon arc;
$O_7, O_8$=a Leitz microscope objective lens F1 x50, 0.85;
$L_2$=a laser purification diaphragm;
$M_7$=a 45° metallized plane mirror.
Outward refraction compensator Ba
$O_4$=a Clairaut (Cerco) lens, f=50 mm, $\phi u$=15 mm;
$P'_3$=3 mm for retina microscopy;
$P_3$=1 mm in medium field work (20° to 30°);
$O_6$=a Nachet microscope objective x6, 215 mm;
$O'_6$=a Nachet microscope objective x19, 215 mm;
$O_2$=a Clairaut (Cerco) lens, f=50 mm, $\phi u$=15 mm.
Optical scanner C
$L_1$=a Melles Griort vitreous reflection separator plate N° 03BPL005;
$M_4$=a General Scanning plane mirror driven by a resonant sinusoidally oscillating electromechanical system (S108);
$M_3$=a General Scanning plane mirror driven by a sawtooth galvanometric system (S116).
Eye transmission optics D
$M_2$=a return metallized plane mirror;
$M_1$=a protected aluminum metallized spherical mirror with a radius of 290 mm;
$P_1$=the patient's pupil.
Return path: refraction compensator Br
$O_1=O_2$;
$M_5$=a 45° return metallized plane mirror;
$O_3=O_4$;
$P_2=P_3$ or $P'_3$.
Detector E
$O_5$=a Clairaut Cerco lens, f=150 mm, $\phi$=30 mm;
T=an image-sized space filter diaphragm;
PM=an RTC photomultiplier model 150 AVP.
Electronics F
Line mirror 109: sinusoidal scan at 8 kHz;
Vertical mirror 116: servo controlled to follow a 50 Hz sawtooth generated at 115;
Video pulse generator 114: a Siemens S178A integrated circuit (ic) having a phase locking loop (S124, 7474) on its output 113;
Sequence generator 113: transistor-transistor logic (TTL) gates types 7400, 7402, 7474;
Analog to digital converter 101: a 4 bit 30 MHz flash converter (TRW inc type TDG 1021 J);
Memories 102 and 103: each memory is one line of 800 four-bit pixels capable of operating at 20 MHz, eg. four Fairchild 93 425A packages;
Digital to analog converter 104: four bits in 7 ns, such as the Analog Devices model HDG 0405 having an output compatible with synchronized video;
Monitor 105: any 625 line TV monitor, with or without an associated video recorder;
Address counters 107 and 108: each comprising a ten-bit counter such as three up/down counter ics type 74S169;
Bus controller: six 74LS244 type ics;
Phase shifters: four times ¼ of a TDB 84;
Sawtooth generator: ¼ of a TDB 84 plus an AD 7512.

The ophthalmoscope obtained in this manner has most advantageous capabilities, in particular for observing details of the retina, including dynamic observation of blood circulation.

For color observation of the retina, the source $S_1$ or $S_2$ emits radiation at least two distinct monochromatic frequencies (or at least in two distinct regions of the spectrum). The remainder of the instrument (FIG. 2) is unchanged, except in so far as $L_1$ is a two (or three) color separator followed by two (or three) distinct detection channels identical to the first. The electronics is modified to operate a color monitor in true or in false color.

It must be emphasized that the ophthalmoscope operates at large pupil aperture, and that it forms images thereof at various points:
in the vicinity of the scanning pair $M_4$, $M_3$;
at $P_2$; and
where applicable at the photomultiplier(s) PM.

The person skilled in the art will understand that separate acquisition of information via two different zones of the pupil can be used to obtain a stereoscopic effect.

We claim:

1. A scanning ophthalmoscope, comprising:
light source means for producing an illuminating beam;
scanning and transmitting means for transmitting the illuminating beam into an eye through a pupil thereof, and for transmitting a return beam from the eye along a coincident optical path with the illuminating beam, said scanning and transmitting means including:
two dimensional scanning means for detecting the illuminating beam over a raster of lines; and
optical means for transmitting the deflected light into the eye, said optical means producing an image of the pupil in the vicinity of said two dimensional scanning means, and for collecting return light from the eye into the return beam, the deflected light and the return light both having a small geometric extent at a level of the pupil and said two-dimensional scanning means deflects the return beam oppositely to the illuminating beam to maintain coincidence of the return beam with the optical path of the illuminating beam; and
eye observing means for collecting the return beam.

2. A scanning ophthalmoscope according to claim 1, wherein said eye observing means includes:
a detection diaphragm conjugated with a point source produced by said light source means and of slightly larger aperture than the size of the image of the said point source; and
a photoelectric transducer placed downstream from the said detection diaphragm.

3. A scanning ophthalmoscope according to claim 2, further comprising a detector lens placed immediately upstream from the said detection diaphragm, which detection diaphragm is placed at a focus of said detector lens, and is followed by said photoelectric transducer.

4. A scanning ophthalmoscope according to claim 2, wherein said optical means for transmitting the deflected light to the eye comprises a spherical mirror used at non-zero incidence.

5. A scanning ophthalmoscope according to claim 4, wherein a raster of the two controlled beam deflectors of said two dimensional scanning means oscillates to produce sinusoidal scanning, and further includes two digital memories and electronic means suitable for digitizing an output signal from said photoelectric transducer, and for filling said two digital memories in opposite order with the digitized signals obtained during go and return half cycles of the sinusoidal oscillation.

6. A scanning ophthalmoscope according to claim 5, wherein the output from said photoelectric transducer is scanned at a variable rate to compensate, at least partially, for the variable excursion speed of the sinusoidal scan.

7. A scanning ophthalmoscope according to claim 4, wherein said two-dimensional scanning means comprises two controlled beam deflectors operating about respective axes of rotation which are collinear with focal axes of astigmatism produced in a spot image of a patient's pupil by said spherical mirror because of the nonzero incidence.

8. A scanning ophthalmoscope according to claim 7, wherein said two controlled beam deflectors comprise pivoting mirrors.

9. A scanning ophthalmoscope according to claim 1, further comprising a beam separator provided upstream from said two dimensional scanning means along the illuminating beam.

10. A scanning ophthalmoscope according to claim 9, further including two similar refraction compensators, one placed on the illuminating path upstream from said beam separator, and the other placed on the observation path downstream from said beam separator, enabling correction of any ametropia of the patient's eye.

11. A scanning ophthalmoscope according to claim 10, wherein each refraction compensator includes a fixed lens, a carriage, a moving lens and an associated diaphragm the carriage bearing the moving lens and associated diaphragm, and the carriages of said two refraction compensators being disposed to move together and conjointly.

12. A scanning ophthalmoscope according to claim 11, wherein the refraction compensator include identical cylindrical lenses in the vicinity of their respective diaphragms.

13. A scanning ophthalmoscope according to claim 11, wherein both the fixed and the moving lenses in the refraction compensators are located between said beam separator and the respective associated diaphragms.

14. A scanning ophthalmoscope according to claim 11, further comprising an inlet lens provided at the inlet end of each refraction compensator on the illumination path to focus at infinity the point source produced by said light source block.

15. A scanning ophthalmoscope according to claim 10, wherein the said iinlet lens is interchangeable to enable said scanning ophthalmoscope to be operated either as a scanning retina microscope or as a medium field observation device, said diaphgrams of said refraction compensators being adjusted in consequence.

16. A scanning ophthalmoscope according to claim 1, wherein said light source means includes a laser or an arc lamp and optical focusing means for providing a point source therefrom.

17. A scanning ophthalmoscope according to claim 16, wherein said light source means includes an optical fiber, at least for medium field work, thereby enabling physical separation of said light block source and the portion of the ophthalmoscope which is close to a patient.

18. A scanning ophthalmoscope according to claim 1, wherein said optical means comprises a mirror.

19. A scanning ophthalmoscope according to claim 1, wherein the deflected light is directed by said scanning means away from the pupil and is deflected by said optical means towards the pupil along an axis of the eye.

* * * * *